United States Patent [19]

Hansson

[11] Patent Number: 5,667,385

[45] Date of Patent: *Sep. 16, 1997

[54] METHOD FOR THE PREPARATION OF IMPLANTS MADE OF TITANIUM OR ALLOYS THEREOF

[75] Inventor: Stig Hansson, Askim, Sweden

[73] Assignee: Astra Aktiebolag, Sodertalje, Sweden

[*] Notice: The term of this patent shall not extend beyond the expiration date of Pat. No. 5,484,286.

[21] Appl. No.: 444,537

[22] Filed: May 19, 1995

Related U.S. Application Data

[62] Division of Ser. No. 39,153, filed as PCT/SE91/00672, Oct. 4, 1991, Pat. No. 5,484,286.

[30] Foreign Application Priority Data

Oct. 8, 1990 [SE] Sweden .................................. 9003206

[51] Int. Cl.$^6$ ...................................... A61C 8/00
[52] U.S. Cl. ...................... 433/201.1; 433/173; 433/174; 623/16; 205/318
[58] Field of Search ................... 433/201.1, 173, 433/174, 175, 176; 623/901, 11, 16; 204/180.2, 181.5; 205/208, 318; 252/62.2; 427/2

[56] References Cited

U.S. PATENT DOCUMENTS

| | | | |
|---|---|---|---|
| 4,145,764 | 3/1979 | Suzuki et al. | 623/16 |
| 4,145,768 | 3/1979 | Suzuki et al. | 623/16 |
| 4,330,891 | 5/1982 | Branemark et al. | 623/16 |
| 5,034,186 | 7/1991 | Shimamune et al. | 623/16 |
| 5,049,074 | 9/1991 | Otani et al. | 433/173 |
| 5,074,881 | 12/1991 | Thull et al. | 623/22 |
| 5,457,672 | 10/1995 | Steinemann et al. | 623/16 |

FOREIGN PATENT DOCUMENTS 0388576  9/1990  European Pat. Off. .

Primary Examiner—Cary E. O'Connor
Attorney, Agent, or Firm—White & Case

[57] ABSTRACT

The invention relates to a method for treating the surface of surgical implants made of titanium or a titanium alloy, for instance dental implants, before implantation in bone tissue. The method results in a roughened exterior implant surface and at the same time a cleaning action is obtained, should there be any contaminants. The surface is blasted with particles of an oxide of titanium, preferably titanium dioxide. In this way an implant having an improved retention in bone tissue is obtained. The Blasted implant is used in a method for treating toothlessness.

6 Claims, No Drawings

METHOD FOR THE PREPARATION OF IMPLANTS MADE OF TITANIUM OR ALLOYS THEREOF

This application is a division of application Ser. No. 08/039,153, filed as PCT/SE91/00672 Oct. 4, 1991, now U.S. Pat. No. 5,484,286.

TECHNICAL FIELD OF THE INVENTION

The present invention relates to a method for treating the surface of surgical implants, particularly dental implants, made of c.p. titanium or of a titanium alloy and intended to be implanted in bone tissue. One object of the invention is to achieve an implant having an improved retention in bone tissue by providing the implant with an improved surface structure. An additional object of the invention is to achieve an implant having a great degree of purity in regard of contaminating substances which may endanger the retention of the implant in the bone tissue. The invention is described below in connection with dental implants, but the invention can be adapted to the surface treatment of other surgical implants to be implanted in bone tissue.

BACKGROUND TO THE INVENTION

The most sensitive part in a dental implant system is the fixture, i.e. that part of the system which is screwed or inserted into a hole in the jaw bone and which thus comes into direct contact with the tissues in the jaw. A suitable material for these implants is titanium. The use thereof as a material in surgical implants was suggested early (for instance by Leventhal et al in the Journal of Bone and Joint Surgery vol 33A, No 2, April 1951).

It is known that the fixture has to be very clean if the ingrowth of the bone tissue onto the implant, the so called osseointegration process, shall function in an optimal way. It even has been maintained that a contamination corresponding to a monomolecular layer could endanger the continued existence of the implant in the tissue.

The structure of the surface of the implant also is important.

The Swedish patent SE-C-416175 (7902035-0) for instance states that a better result of an implant operation is achieved if an implant with a surface of titanium oxide is provided with pores having a size of 10–1000 nm defined as being "micropits". This patent specification does however not clearly show how this surface differs from other known surfaces, for instance turned surfaces, or to what extent the retention of the implant is improved.

Several other publications have discussed the importance of the surface roughness for the retention of the implant, for instance the academic treatise by Jan Lundskog: "Heat and Bone Tissue" Laboratory of Experimental Biology, Department of Anatomy, University of Gothenburg, Sweden 1972, the article "Adhesion of bone to titanium", by S. G. Steinemann, J. Eulenberger, P.-A. Maeusli and A. Schroeder in Biological and Biomechanical Performance of Biomaterials, edited by P. Christel, A. Meunier and A. J. C. Lee, Elsevier Science Publishers B. V., Amsterdam 1986 and the article "Removal Torques for Polished and Rough Titanium Implants", Carlsson L., Röstlund T., Albrektsson B., Albrektsson T., Int J Oral Maxillofac Implants, 1988; 3:21–24. These publications indicate that it may be better with an implant surface having larger (macroscopic) irregularities or pores than those described in the above Swedish patent.

Implants have been made by cutting operations for a long time, primarily by turning. According to the above Swedish patent such a machining may result in a surface with microscopic irregularities. Several cleaning methods have been suggested and used, such as cleaning with organic solvents, electropolishing, sand blasting and treatment with alkalic and acid solutions.

One commonly used cleaning method thus is blasting with well known blasting agents, such as sand or aluminium oxide. Blasting with a blasting material having correctly sized particles results in the surface roughness which is desired in order to obtain a good mechanical retention in the bone. One problem with blasting the surface of the fixture is however that, although the existing contaminations may be removed, residues from the blasting agent may remain on the surface of the implant. The blasting agents commonly used, for instance aluminium oxide, thus may result in contaminations that are impossible or very difficult to remove in a subsequent cleaning process.

DESCRIPTION OF THE INVENTION

The object of the invention is to provide a treatment of implants made of titanium or titanium alloys which in one operation both ensures that the surface of the implant is clean and that the surface has the macroscopic structure which is necessary for a good retention of the implant in the jaw bone.

According to the present invention this is achieved in that implants of titanium or of an alloy of titanium are blasted with particles of an oxide of titanium, preferably titanium dioxide. Since titanium exposed to air has a chemically resistant layer of oxide, the most important one being titanium dioxide, the blasting operation will not introduce any foreign, contaminating material onto the implant surface, although effectively removing existing contaminations and providing the desired roughness.

In accordance with a preferred embodiment of the invention the oxide used for the the blasting comprises titanium dioxide.

In a further preferred embodiment of the invention, the oxide, which preferably comprises titanium dioxide, comprises particles having a grain size within the range of 1–2000 µm, more preferably particles having a grain size within the range of 1–300 µm. In another preferred embodiment the particles have a grain size within the range of 1–50 µm. Particles having a size being close to the upper limit preferably are used in the treatment of larger orthopaedic prostheses.

It has proved that the fixture obtains a surprisingly good force-transmitting capacity in implants whose surface have been treated in accordance with the invention. This is important since the fixture is subjected to considerable forces which are to be transmitted to the bone. The fixture therefore has to have a design which allows a safe transmission of these forces to the bone. As indicated above, the strength of the bond between the bone and the implant is improved if the surface of the fixture has a macroscopic roughness which is superimposed on the geometrical design of the fixture. The use of blasting particles having a size of 1–50 µm results for instance in a size of the irregularities on the surface of the implant in the range 1–25 µm (the size of the irregularities are normally smaller than the size of the particles). Smaller irregularities may of course also be superimposed on these irregularities. In this range of the size of the roughness, the strength of the bond implant—bone is considerably improved. It has been shown that this strength-improving effect is reduced if the size is reduced.

The strength-improving effect is negligible at sizes below 0.3 µm. Larger irregularities, 5–200 µm, result in an additional improvement of the strength of the bond implant—bone, but irregularities in the size range 100–200 µm may in some cases interfere negatively with the geometrical design of the implant. The size of the irregularities here can be defined as an approximative diameter or width of a rounded respectively an oblong shape.

EXAMPLES

A. Fixtures made of titanium of the kind used by the applicant, AB Astra (Astra Meditec), were thoroughly cleaned and degreased in a conventional manner and were then blasted in a blasting equipment "Sandmaster, Ultrafine Sandblaster Type FG3-82, Wülsag, Zofingen, Switzerland". A titanium dioxide powder having a grain size of 10–53 µm was used ("Metco 102", Metco Scandinavia AB, Varby, Sweden, normally used for plasma- or flame-spraying). Air was used as carrying medium in the blasting process. Each fixture was blasted about 20 seconds. The fixture was rotated and the blasting nozzle was moved up and down along the longitudinal axis of the fixture at an angle of about 90 degrees relative to the longitudinal axis of the fixture. The air pressure of the apparatus was set at 1 Bar (100 kPa) above atmospheric pressure.

Some of the blasted fixtures were examined in an electron microscope. A rough, irregular surface was observed. The size of the irregularities were about 5–15 µm with superimposed irregularities having a smaller size.

The implants were then washed in organic solvents and a number of fixtures were examined by means of ESCA (Electron Spectroscopy for Chemical Analysis) in order to study the degree of cleanliness. The implants proved to be exceptionally clean.

B. The above experiment was repeated with another blasting equipment, "Abrasive Blaster, Mark 3", delivered by Belle de St Claire, 16147 Valerio St, Van Nuys, Calif. 91406, U.S.A. Blasting agent and carrying medium were the same as above. The air pressure of the apparatus was set at 80 psi (5,5 bar, 550 kPa). Again a dental implant fixture from Astra Meditec was blasted. The blasting nozzle was moved axially up and down the surface of the implant about 5–10 mm away from the the surface. The fixture was simultaneously rotated. The nozzle then was moved over the outer lower end of the fixture. Duration about 20 seconds. Visually the fixture displayed a dull surface after the blasting. During an examination under a microscope it proved that the blasting had resulted in a rough surface.

ANIMAL TESTS

I. Histological analysis.

10 fixtures, which had been blasted in accordance with the above Example A, were operated into the upper jaw of Beagle dogs together with untreated control fixtures. A histological analysis after 2 respectively 4 months showed that the blasted implants had been osseo-integrated in the same way as the. untreated control fixtures.

II. Summary of results obtained in animal studies relating to osseointegration and fixation strength of "smooth" respectively blasted surface of titanium implants.

The geometrical design and the surface (macro-, microstructure) of an implant are two factors considered important for the osseointegration. In order to study these factors and the differences in the degree of the osseointegration and the strength of the fixation two studies comprising threaded and cylindrical implants having smooth alternatively blasted surfaces were made.

STUDY 1

The study comprised 3 dogs (labrador) which each had 6 threaded fixtures implanted (i.e. 18 in all). Of these 18 fixtures 9 had a conventional structure of the surface whereas the remaining 9 fixtures had been treated with a blasting method in accordance with the above Example A.

After a healing period of 1 respectively 6 months for both implant surfaces a torque test was performed in which the fixtures were screwed out and the torque which was necessary for this was registered with a torque meter.

The results were that the fixtures having conventional surfaces could be removed when torques in the range of 35–45 Ncm were applied. The fixtures which had been blasted could not be removed although a torque of 100 Ncm was applied. The testing equipment broke at torques exceeding 100 Ncm.

STUDY 2

In this animal study both cylindrical and threaded fixtures having alternatively conventional surfaces and surfaces blasted according to the Example were compared in accordance with the following schedule:

Cylindrical implant, conventional surface: 6 fixtures
Cylindrical implant, blasted surface: 6 fixtures
Threaded implant, conventional surface: 6 fixtures
Threaded implant, blasted surface: 6 fixtures The 24 fixtures were implanted in 6 dogs, 4 in each, in accordance with a random schedule.

The result was that all the fixtures having a conventional surface could be removed at torques ranging from 30 to 40 Ncm. The blasted implants, both the threaded and the cylindrical ones, could however not be removed despite the application of torques of 100 Ncm. The equipment could not stand higher torques.

The conclusion is that the blasted surface gives a considerably higher strength in the bond titanium—bone.

As mentioned in the introduction, it should be understood that the present invention only has been illustrated by means of dental implants and that the method according to the invention of course is applicable to all kinds of bone implants having a surface to be implanted made of titanium or titanium alloys.

It further should be pointed out that, although the invention has been illustrated using air blasting, airless (mechanical) blasting and wet blasting also can be used.

I claim:

1. An implant having a contaminant-free surface produced by the process of blasting the surface with particles of titanium oxide, wherein the surface is free from any contaminants after it has been blasted.

2. An implant comprising titanium or an alloy thereof and having a contaminant-free surface, said implant produced by the process of blasting the surface with particles of titanium oxide, wherein the surface is free from any contaminants after it has been blasted.

3. The implant of claim 2, wherein the particles are titanium dioxide.

4. The implant of claims 2 or 3, wherein the particles have a size in the range of 1 to 2000 µm.

5. The implant of claim 4, wherein the particles have a size in the range of 1 to 300 µm.

6. The implant of claim 5, wherein the particles have a size in the range of 1 to 50 µm.

* * * * *